United States Patent
Zhang

(10) Patent No.: US 9,944,938 B2
(45) Date of Patent: Apr. 17, 2018

(54) CONSTITUTIVE SOYBEAN PROMOTERS

(71) Applicant: Bayer CropScience LP, Research Triangle Park, NC (US)

(72) Inventor: Shirong Zhang, Raleigh, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 14/767,599

(22) PCT Filed: Mar. 11, 2014

(86) PCT No.: PCT/US2014/023291
§ 371 (c)(1),
(2) Date: Aug. 13, 2015

(87) PCT Pub. No.: WO2014/150449
PCT Pub. Date: Sep. 25, 2014

(65) Prior Publication Data
US 2015/0376643 A1 Dec. 31, 2015

Related U.S. Application Data

(60) Provisional application No. 61/790,907, filed on Mar. 15, 2013.

(51) Int. Cl.
*C12N 15/82* (2006.01)
*C07K 14/415* (2006.01)
*A01H 5/10* (2018.01)

(52) U.S. Cl.
CPC .......... *C12N 15/8216* (2013.01); *A01H 5/10* (2013.01); *C07K 14/415* (2013.01); *C12N 15/8273* (2013.01); *C12N 15/8274* (2013.01); *C12N 15/8279* (2013.01)

(58) Field of Classification Search
None
See application file for complete search history.

(56) References Cited

U.S. PATENT DOCUMENTS

| 8,395,021 B2 * | 3/2013 | Finer | C12N 15/8216 800/278 |
| 2010/0186119 A1 * | 7/2010 | Finer | C12N 15/8241 800/287 |
| 2010/0186127 A1 * | 7/2010 | Byrum | C07K 14/415 800/298 |
| 2014/0007289 A1 * | 1/2014 | Kuhn | C12N 15/8222 800/278 |

FOREIGN PATENT DOCUMENTS

WO   WO 2012/127373   *   9/2012   ........... C12N 15/113

OTHER PUBLICATIONS

Maiti et al. Promoter/leader deletion analysis and plant expression vectors with the figwort mosaic virus (FMV) full length transcript (FLt) promoter containing single or double enhancer domains. (1997) Transgen. Res., vol. 6; pp. 143-156.*
Donald et al. Mutation of either G box or I box sequences profoundly affects expression from the *Arabidopsis* rbcS-1A promoter. (1990) EMBO J.; vol. 9; pp. 1717-1726.*
Benfey et al. The cauliflower mosaic virus 35S promoter: combinatorial regulation of transcription in plants. (1990) Science; vol. 250; pp. 959-966.*
Kim et al. A 20 nucleotide upstream element is essential for the nopaline synthase (nos) promoter activity. (1994) Plant Mol. Biol.; vol. 24; pp. 105-117.*

* cited by examiner

*Primary Examiner* — Cathy Kingdon Worley

(57) ABSTRACT

The present invention provides compositions and methods for regulating expression of heterologous nucleotide sequences in a plant. Compositions include two novel promoter nucleotide sequences for the genes encoding gamma tonoplast intrinsic protein and plasma membrane intrinsic protein in soybean, as well as vectors, microorganisms, plants and plant cells comprising the promoter nucleotide sequences, or variants and fragments thereof. Methods for expressing a heterologous nucleotide sequence in a plant using the promoter sequences disclosed herein are also provided. The methods comprise stably incorporating into the genome of a plant cell a nucleotide sequence operably linked to the promoter of the present invention and regenerating a stably transformed plant that expresses the nucleotide sequence.

20 Claims, 1 Drawing Sheet

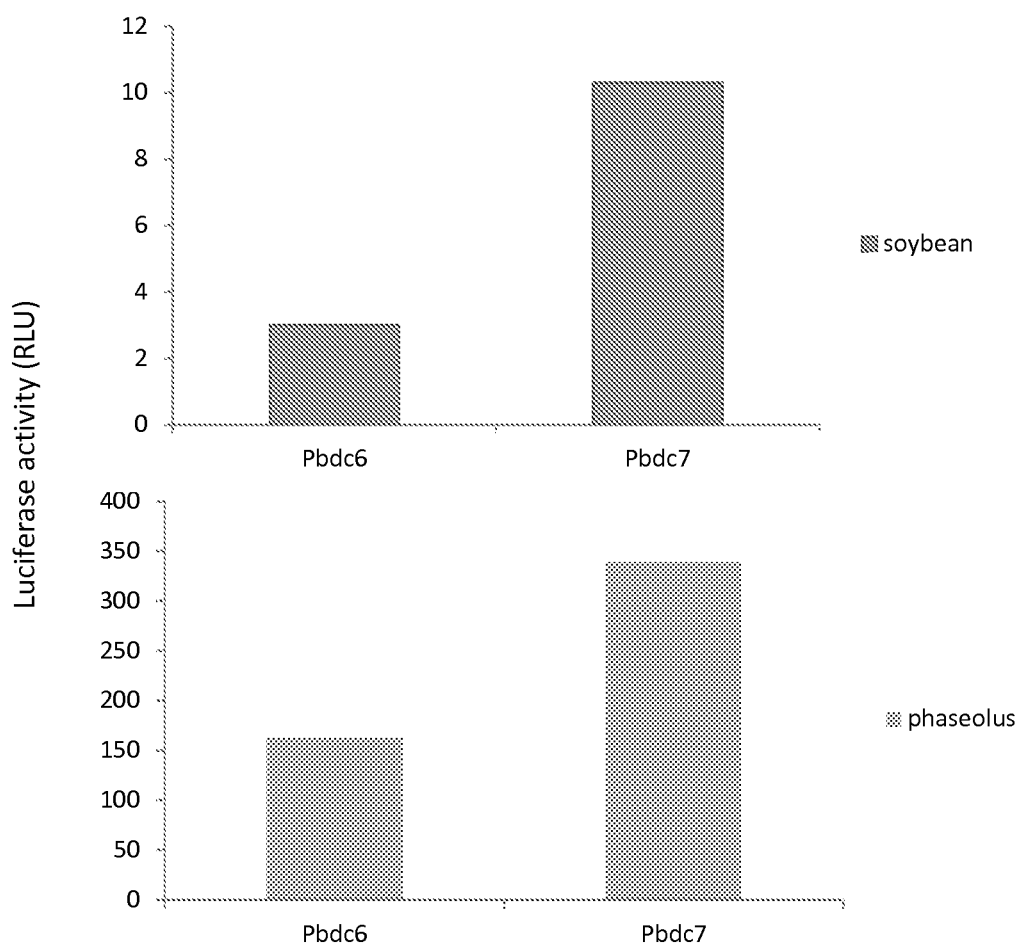

SEQUENCE LISTING

```
<160> NUMBER OF SEQ ID NOS: 2

<210> SEQ ID NO 1
<211> LENGTH: 1230
<212> TYPE: DNA
<213> ORGANISM: Glycine max

<400> SEQUENCE: 1
ctcgaaacag aatatagcag tgattccagg tgcacggtgc cacctgtttg ctaaaaaaca      60
aaaataattg aggggggttaa ctaagctaat ccaaaccaga gatcagagcg ggagattaat     120
tttaataatt ctcttagtct cttcattaag atcctttttt tcatatcaag ttaaacttta     180
tgcaaaatat catattttca tttcagaaaa acaaaaaagc tactgtacat acaacattaa     240
gtttaaaata aacaagtaca gtttacccac gtgtcagtcg cggtcttgta ataatacctg     300
cttttttccg gtgggtcacc agagagtcac agtgcttatc cccttatctc attcattata     360
ttatgatgaa ttatgcccctt ataattatag attaactact actttgcagt tataaactta     420
aaattcacaa ttctctctat tatttctttg cacacgcgat ataatataaa actctagagc     480
```

| | |
|---|---|
| tatcgtcatt cacaacttta aaaaaattaa aaaagttaat tatattagag tgcaatagct | 540 |
| cactctcttt ctctcacgga accatccaga tatacaaaaa agactagaca atgtccactt | 600 |
| atcagcgccc tacatggctc ttatccatct cggacacgtg tcagtcctgg gacggctctg | 660 |
| gcccaaacga ttcgctgtct taagagcaac caacagtgat gtggggatat actccttgtt | 720 |
| ttttttttct tcaaataatt atgtataatg tatttataat ataattttttt tacttttaaa | 780 |
| ataattattc tgtatagttt cgatgataat ttatgctaaa tgtttatgta aaattattta | 840 |
| cactttttaa tacatagaca ttaactttttt ttctctcata aatgtttaaa ataaaaggaa | 900 |
| aaacaattaa taatttgaaa tgaagaacct gtcccaggct gtcaccaaat aggattcttt | 960 |
| cttttccggc ttggtgtttt tgaaaaactt gattcctgac attttttggaa gcattgcgca | 1020 |
| tattttccaa ataggaaaat aaaaataacc gggaaccggg tacagccggt ggaatcctag | 1080 |
| gcaggctcgt cttcaatcac ggtatataag aagctacgaa gcgaaaacga atagcatagc | 1140 |
| gaaacagaga gtggtttcag tgagtgatcg gtgttcactt gatccttcat aagtcgtcat | 1200 |
| catcatcatc atcatcaccg ttgattgaag | 1230 |

```
<210> SEQ ID NO 2
<211> LENGTH: 1688
<212> TYPE: DNA
<213> ORGANISM: Glycine max

<400> SEQUENCE: 2
```

| | |
|---|---|
| ctaacgtttt tggctcacaa ctcaaactga tcaagaacct ttcattttat taacgttatc | 60 |
| cttacaagtc actcagacta atcaaggcac taaactaatg catattaggt aatgcaaata | 120 |
| aataatgacg ctcccatgaa tattcaaatg gtttcttttg cttttttgctt aacgactttt | 180 |
| gtatctctac gaattacttg agaaaaagct gctattatta ttatccaact atataaacaa | 240 |
| atgaaagcta cagttaagga catggcctat taacaatata tgtagacttg atcattgtct | 300 |
| catccacgag atagaaacaa atatatataaa agggctcatt atgcttatttt agttcaagga | 360 |
| agagaggaaa atgagttatg catgtagcca gaatgaacat ttgatcatgg acgtgagata | 420 |
| agttaatcgc tgacagccat gtgccgacca tgtttttata aatgaaaaga aagaaagaaa | 480 |
| tgttcgtata taataattta cgggcacaag aaccttgtta ataattatca ttatctttttt | 540 |
| ttttttttctg aaaaccttgt ttctctaatc attgatgtat atttgtaatc tctctccaac | 600 |
| tccttaccat gtagtgagga gtgaatttca tattaacatt ggtcattaca atattatcaa | 660 |
| ctttcgcgct aaatcagaat atatataaac tttcgcgcta atatattctta aaatattggt | 720 |
| attttggtag gtaaagattt acaatcacga ataagtaata aagaattttt catacgcatt | 780 |
| caatgattcc gaccatgtgt tatttgtttt gaaatacctaa tatgagagac tgagagcatc | 840 |
| ttgttattta tgactgctta ttaattttcc cttcatgcct tatctaatta gtttaaatat | 900 |
| attatttctc cttgtataaa aaaaaattat gatttctcca accatacata ttagagaata | 960 |
| acttgaaatt atattcaacg tattaattgc attaccttta acgtgccaaa ataataaata | 1020 |
| aaactaaaaa ctactacaat cataaatcgc gtgtggttga attgagacaa attctattct | 1080 |
| aaaaaagaaa aacattaaca aaaagagaaa gaaaaaaaaa attgttgaca cctgacagcg | 1140 |
| gtaacaggga agtagcggta ggagattggc gtgtcggttt ccaactctgg aatccaacgt | 1200 |
| gccaaactga gaatgcagga gaaagagaca cgtgtccaat tgcaggcgcg agttcaacgt | 1260 |
| gacaattcga aagccttgac aatcgcaccg cccagcatcg aacgcagaca aggaccacgt | 1320 |
| ggaattcggt ccctgtatcc gtcaaaacgt tttttaccct cttcttcttc agttcttcca | 1380 |

```
tttttatttt tttttcaaac cacagtaatc cacgttccag tgctgcgcgg aacatggtcg    1440
gtctttctag gagtggttgg aatcccgcca gctaggacaa accccatcaa tcattggtcc    1500
ccatcaaaca aaaacatttt taaaaattca acatattacg ccacgggacc cacctcccac    1560
cacccctcac cctcacttct attaactcaa acctattccg gttataaatc cgcaaccctc    1620
gttcttacta actcactcac tcacaactca gtgaaagaga atccgaggcg aagagaagag    1680
aaaaatta                                                             1688
```

CONSTITUTIVE SOYBEAN PROMOTERS

CROSS REFERENCE TO RELATED APPLICATION

This application claims the benefit of U.S. Provisional Application Ser. No. 61/790,907, filed Mar. 15, 2013, the contents of which are herein incorporated by reference in their entirety.

REFERENCE TO SEQUENCE LISTING SUBMITTED ELECTRONICALLY

A copy of the sequence listing is submitted electronically via EFS-Web as an ASCII formatted sequence listing with a file named "2912939-20179WO01_Sequence_Listing.txt", created on Mar. 10, 2014, and having a size of 4.14 kilobytes and is filed concurrently with the specification. The sequence listing contained in this ASCII formatted document is part of the specification and is herein incorporated by reference in its entirety.

FIELD OF THE INVENTION

The present invention relates to the field of plant molecular biology, more particularly to the identification and use of regulatory elements in plants.

BACKGROUND OF THE INVENTION

Currently, there is a high demand for transgenic plants that express biotechnologically important protein products at a high or inducible level. Manipulation of crop plants to alter and/or improve phenotypic characteristics (such as productivity or quality) requires the expression of heterologous genes in plant tissues. Such genetic manipulation has become possible by virtue of two discoveries: the ability to transform heterologous genetic material into a plant cell and by the existence of promoters that are able to drive the expression of the heterologous genetic material.

Among the most commonly used promoters are the nopaline synthase (NOS) promoter (Ebert et al., Proc. Natl. Acad. Sci. U.S.A. 84:5745-5749 (1987)); the octapine synthase (OCS) promoter, caulimovirus promoters such as the cauliflower mosaic virus (CaMV) 19S promoter (Lawton et al., Plant Mol. Biol. 9:315-324 (1987)); the CaMV 35S promoter (Odell et al., Nature 313:810-812 (1985)), and the figwort mosaic virus 35S promoter (Sanger et al., Plant Mol. Biol. 14:433-43 (1990)); the light inducible promoter from the small subunit of rubisco (Pellegrineschi et al., Biochem. Soc. Trans. 23(2):247-250 (1995)); the Adh promoter (Walker et al., Proc. Natl. Acad. Sci. U.S.A. 84:6624-66280 (1987)); the sucrose synthase promoter (Yang et al., Proc. Natl. Acad. Sci. U.S.A. 87:4144-4148 (1990)); the R gene complex promoter (Chandler et al., Plant Cell 1:1175-1183 (1989)); the chlorophyll a/b binding protein gene promoter; and the like.

The identification and isolation of regulatory elements useful for strong or inducible expression of genes in microorganisms and plants would be beneficial in the development of commercial varieties of transgenic plants.

SUMMARY OF INVENTION

Compositions and methods for regulating gene expression in a plant are provided. Compositions comprise nucleotide sequences from *Glycine max* and variants thereof that initiate transcription in a plant. Specifically, a transcriptional initiation region isolated from a gamma tonoplast and a plasma membrane gene of *Glycine max* is provided. Further compositions of the invention comprise the nucleotide sequences set forth in SEQ ID NO:1 and 2, and variants and fragments thereof. Compositions of the present invention also include expression cassettes comprising a promoter of the invention operably linked to a heterologous nucleotide sequence of interest. The invention further provides vectors comprising the expression cassettes, and plants and plant cells having stably incorporated into their genomes an expression cassette described above. Additionally, compositions include transgenic seed of such plants.

Operably linked to the promoter is a sequence of interest that may modify the phenotype of the plant. Such modification may include, for example, modulating the production of an endogenous product, or it may include production of an exogenous expression product to provide for a novel function or product in the plant. For example, a heterologous nucleotide sequence that encodes a gene product that confers herbicide or pest resistance is encompassed.

DESCRIPTION OF FIGURES

FIG. 1 shows high level of expression of luciferase of when under the control of the Pbdc6 (SEQ ID NO:1) and the Pbdc7 (SEQ ID NO:2) promoters.

DETAILED DESCRIPTION

The present invention is drawn to compositions and methods for regulating gene expression in plants or plant cells. The compositions of the present invention comprise novel nucleotide sequences for the soybean promoters. In particular, the present invention provides for isolated promoter nucleic acid molecules comprising the nucleotide sequence set forth in SEQ ID NO:1 or 2, as well as fragments and variants thereof. In addition, transformed plants, plant cells, and seeds are provided.

The promoter sequences of the invention, when assembled within a DNA construct such that the promoter is operably linked to a nucleotide sequence of interest, drive expression of the nucleotide sequence in the cells of an organism stably transformed with this DNA construct, particularly plant cells. The promoter sequences are also useful as probes for the isolation of other soybean promoter sequences or genes, as molecular markers, and the like.

Methods for expressing a nucleotide sequence in a plant comprise introducing into plant cells an expression cassette comprising a promoter of the invention operably-linked to a nucleotide sequence of interest, and regenerating a transformed plant from the plant cell.

The articles "a" and "an" are used herein to refer to one or more than one (i.e., to at least one) of the grammatical object of the article. By way of example, "an element" means one or more elements.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule, or biologically active portion thereof, is substantially free of other cellular material, or culture medium when produced by recombinant techniques, or substantially free of chemical precursors or other chemicals when chemically synthesized.

Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the promoter molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. Various aspects of the invention are described in further detail in the following subsections.

Isolated Nucleic Acid Molecules, and Variants and Fragments Thereof

Nucleotide sequences of the present invention include the promoter sequences set forth in SEQ ID NO:1 and 2, and variants thereof. By "promoter" is intended a nucleic acid sequence that functions to direct transcription of a downstream coding sequence. A promoter generally comprises a DNA sequence homologous to the consensus 5'-TATAAT-3' (TATA box) about 10-30 base pairs 5' to the transcription start (cap) site that is capable of directing RNA polymerase to initiate RNA synthesis. Promoters may further comprise other recognition sequences, generally upstream or 5' to the TATA box, referred to as upstream promoter elements, which influence the transcription initiation rate. These include the CAAT box, which is often found about 30 to 70 base pairs 5' to the TATA box and has homology to the canonical form 5'-CCAAT-3' (Breathnach and Chambon (1981) *Ann. Rev. Biochem.* 50:349-383). In plants the CAAT box is sometimes replaced by a sequence known as the AGGA box, a region having adenine residues symmetrically flanking the triplet G(orT)NG (Messing et al. (1983), in *Genetic Engineering of Plants*, T. Kosuge, C. Meredith and A. Hollaender (eds.), Plenum Press, New York, pp. 211-227). These elements, together with other transcriptional and translational regulatory nucleic acid sequences (also termed "control sequences"), are necessary for the expression of a DNA sequence of interest. Methods for isolating and identifying regulatory elements not described herein, such as enhancers and elements responsible for tissue or temporal expression of the coding region, are well known in the art. See, for example U.S. Pat. Nos. 5,635,618; 6,218,140; 6,303,370; 6,310,197; and 6,355,864.

By "core promoter" is intended a promoter without promoter elements. A core promoter contains essential nucleotide sequences for promoter function, including the TATA box and the initiation site of transcription. Such a region is normally present, with some variation, in most promoters. The core promoter region is often referred to as a minimal promoter region because it is functional on its own to promote a basal level of transcription. In various embodiments, the core promoter sequence for Pbdc6 corresponds to approximately nucleotides 29 through 318 of SEQ ID NO:1; the TATA corresponds to approximately nucleotides 288 through 296 of SEQ ID NO:1; and the translation initiation site corresponds to nucleotide position 318 of SEQ ID NO:1. In other embodiments, the core promoter sequence for Pbdc7 corresponds to approximately nucleotides 1341 through 1643 of SEQ ID NO:2; the TATA corresponds to approximately nucleotides 1603 through 1608 of SEQ ID NO:2; and the translation initiation site corresponds to nucleotide position 1643 of SEQ ID NO:2. It will be understood by one of skill in the art that the core promoter region may differ from the above-referenced positions by 1, 2, 3, 4, 5, 6, 7, 8, 9, 10 or more nucleotides upstream or downstream, and that variations within the core promoter sequence may be tolerated.

Nucleic acid molecules that are fragments of the disclosed promoter sequences are also encompassed by the present invention. By "fragment" is intended a portion of the promoter sequence. A fragment of a nucleotide sequence may be biologically active and hence be capable of initiating transcription of an operably-linked nucleotide sequence in a plant, or it may be a fragment that can be used as a hybridization probe or PCR primer using methods disclosed below. Assays to determine whether such fragments decrease expression levels or alter the nature of expression, i.e., constitutive or inducible expression are well known in the art.

Nucleic acid molecules that are fragments of a promoter sequence may comprise at least about 20, 50, 100, 200, 300, 400, 500, 600, 700, 800, 900, 1000, 1100, 1200, 1300, 1400, 1500, 1600 contiguous nucleotides, or up to the number of nucleotides present in a full-length promoter sequence disclosed herein (for example, 1230 nucleotides for SEQ ID NO:1, or 1688 nucleotides for SEQ ID NO:2) depending upon the intended use. By "contiguous" nucleotides is intended nucleic acid residues that are immediately adjacent to one another. Biologically active fragments of the promoters of the present invention will retain promoter activity (i.e., initiating transcription). By "retains promoter activity" is intended that the fragment will have at least about 30%, at least about 50%, at least about 70%, or at least about 80% of the promoter activity of the full-length promoter. A biologically active portion of a promoter can be prepared by isolating a portion of one of the promoter nucleotide sequences of the invention and assessing the activity of that portion of the promoter. Methods for measuring promoter activity are well known in the art. See the section entitled "Evaluation of Promoter Activity" for examples of suitable methods.

Such fragments will generally comprise the TATA recognition sequence of the particular promoter sequence. These fragments may be obtained by cleaving the naturally occurring promoter nucleotide sequence disclosed herein with restriction enzymes, by synthesizing a nucleotide sequence from the naturally occurring sequence of the promoter DNA sequence, or through the use of PCR technology. See particularly, Mullis et al. (1987) *Methods Enzymol.* 155:335-350, and Erlich, ed. (1989) *PCR Technology* (Stockton Press, New York). Variants of these promoter fragments, such as those resulting from site-directed mutagenesis, are also encompassed by the compositions of the present invention.

Variants of the promoter sequences disclosed herein are also encompassed. By "variant" is intended a sufficiently identical sequence. Promoter sequences encompassed by the present invention are sufficiently identical to the nucleotide sequence of SEQ ID NO:1 or 2. By "sufficiently identical" is intended a nucleotide sequence that has at least about 70% or 75%, about 80% or 85% sequence identity, about 90%, 91%, 92%, 93%, 94%, 95%, 96%, 97%, 98% or 99% sequence identity compared to a reference sequence using one of the alignment programs as described herein.

Naturally occurring variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still have promoter activity as defined herein.

Variants encompassed by the present invention are biologically active, that is they continue to possess the desired biological activity of the native sequence, that is, retaining promoter activity (i.e., initiating transcription). By "retains promoter activity" is intended that the variant will have at least about 30%, at least about 50%, at least about 70%, or at least about 80%, or higher, of the promoter activity of the native sequence. Methods for measuring promoter activity are well known in the art. See the section entitled "Evaluation of Promoter Activity" for examples of suitable methods.

The skilled artisan will further appreciate that changes can be introduced by mutation into the nucleotide sequences of the invention without altering the ability of the promoter to drive expression in a plant cell. Thus, variant isolated nucleic acid molecules can be created by introducing one or more nucleotide substitutions, additions, or deletions into the corresponding nucleotide sequence disclosed herein. Mutations can be introduced by standard techniques, such as site-directed mutagenesis and PCR-mediated mutagenesis. Such variant nucleotide sequences are also encompassed by the present invention.

Alternatively, variant nucleotide sequences can be made by introducing mutations randomly along all or part of the promoter sequence, such as by saturation mutagenesis, and the resultant mutants can be screened for ability to drive expression of an operably linked nucleotide sequence in a plant cell.

By "operably linked" is intended a functional linkage between a promoter and a second sequence, wherein the promoter sequence initiates and mediates transcription of the DNA sequence corresponding to the second sequence. Generally, but not always, operably linked means that the nucleic acid sequences being linked are contiguous and, where necessary to join two protein coding regions, contiguous and in the same reading frame.

To determine the percent identity of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN program of Altschul et al. (1990) *J. Mol. Biol.* 215:403. BLAST nucleotide searches can be performed with the BLASTN program, score=100, wordlength=12, to obtain nucleotide sequences homologous to promoters of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTN) can be used. See, www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the DNA sequence, and thus can provide data about the sequence conservation of the entire nucleotide sequence. The ClustalW algorithm is used in several commercially available DNA analysis software packages, such as the ALIGNX module of the vector NTi Program Suite (Informax, Inc). A non-limiting example of a software program useful for analysis of ClustalW alignments is GeneDoc™. Genedoc™ (Karl Nicholas) allows assessment of DNA similarity and identity between multiple genes. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA).

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

Using methods such as PCR, hybridization, and the like, corresponding sequences from other organisms, particularly other plants, can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY). Sequences identified by their identity to the promoter sequences set forth herein are encompassed by the present invention.

Oligonucleotide primers can be designed for use in PCR reactions to amplify corresponding DNA sequences from cDNA or genomic DNA from a plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Cold Spring Harbor, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, and partially-mismatched primers.

In a hybridization method, all or part of a known nucleotide sequence can be used to screen cDNA or genomic libraries. Methods for construction of such cDNA and genomic libraries are generally known in the art and are disclosed in Sambrook and Russell, 2001, supra. The hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known promoter sequence disclosed herein. Degenerate primers designed on the basis of conserved nucleotides in the nucleotide sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of the promoter sequence of the invention or a fragment or variant thereof. Preparation of probes for hybridization is generally known in the art and is disclosed in Sambrook and Russell, 2001, supra, herein incorporated by reference.

For example, the entire promoter sequence disclosed herein, or one or more portions thereof, may be used as a probe capable of specifically hybridizing to corresponding promoter-like sequences. To achieve specific hybridization under a variety of conditions, such probes include sequences that are unique and are at least about 10 nucleotides in length, or at least about 20 nucleotides in length. Such probes may be used to amplify corresponding promoter sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. Optionally, wash buffers may comprise about 0.1% to about 1% SDS.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)–0.61 (% form)– 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration can be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated sequences that have promoter activity and which hybridize under stringent conditions to the promoter sequences disclosed herein, or to fragments thereof, are encompassed by the present invention.

Methods of Use

Methods of the present invention are directed to expressing heterologous nucleotide sequences in plants and plant cells under the control of the promoter sequence of the present invention. The transgenic plants may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified ability to utilize, partition and/or store nitrogen, and the like. These results can be achieved through the expression of heterologous genes or by the increased expression of endogenous products in plants. Alternatively, the results can be achieved by reducing the expression of one or more endogenous products, particularly enzymes, transporters, or cofactors, or affecting nutrient uptake in the plant.

Generally, the nucleotide sequence for the promoter of the invention is provided in an expression cassette with a nucleotide sequence of interest, typically a heterologous nucleotide sequence, for expression in the plant of interest. By "heterologous nucleotide sequence" is intended a sequence that is not naturally operably-linked with the promoter sequence, including non-naturally occurring multiple copies of a naturally occurring DNA sequence. While this nucleotide sequence is heterologous to the promoter sequence, it may be homologous, or native, or heterologous, or foreign, to the plant host. It is recognized that the promoter may also drive expression of its homologous or native nucleotide sequence. In some cases, the transformed plant may have a change in phenotype. Heterologous nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Any sequence of interest may be expressed by the promoter sequences of the invention. Such heterologous nucleotide sequences include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition.

More specific genes of interest for the present invention include, but are not limited to, genes that improve crop yield, genes that improve desirability of crops, genes encoding proteins conferring resistance to abiotic stress, such as drought, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. It is recognized that any gene of interest can be operably linked to the promoter sequences of the invention and expressed in a plant.

These heterologous nucleotide sequences may encode proteins involved in providing disease or pest resistance. By "disease resistance" or "pest resistance" is intended that the plants avoid the harmful symptoms that are the outcome of the plant-pathogen interactions. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Examples of genes of interest may be found, for example, at www.nbiap.vt.edu/cfdocs/fieldtests2.cfm.

"Pest" includes, but is not limited to, insects, fungi, bacteria, viruses, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include but are not limited to *Pratylenchus* spp. Fungal pests include those that cause leaf, yellow, stripe and stem rusts.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene) or other such genes known in the art.

Genes that improve crop yield include dwarfing genes, such as Rht1 and Rht2 (Peng et al. (1999) *Nature* 400:256-261), and those that increase plant growth, such as ammonium-inducible glutamate dehydrogenase. Genes that improve desirability of crops include, for example, those that allow plants to have a reduced saturated fat content, those that boost the nutritional value of plants, and those that increase grain protein. Genes that improve salt tolerance are those that increase or allow plant growth in an environment of higher salinity than the native environment of the plant into which the salt-tolerant gene(s) has been introduced.

Methods for identifying regulatory elements (e.g., promoters, terminators and enhancers) are also provided. By "regulatory element" or "regulatory region" is intended a portion of nucleic acid found upstream or downstream of a gene, that may be comprised of either DNA or RNA, or both DNA and RNA and that is involved in gene expression. Regulatory elements may be capable of mediating organ specificity, or controlling developmental or temporal gene activation and include promoter elements, core promoter elements, elements that are inducible in response to an external stimulus, elements that are activated constitutively, transcriptional terminators, polyadenylation signals, and elements that decrease or increase promoter activity such as negative regulatory elements or transcriptional enhancers, respectively. By "cis-acting" is intended a sequence that is physically contiguous with the transcribed sequence. Cis-acting sequences typically interact with proteins or other molecules to carry out (turn on/off, regulate, modulate, etc.) transcription. By "transcriptional enhancer" is intended a nucleic acid sequence that, when positioned proximate to a promoter and present in a transcription medium capable of supporting transcription, confers increased transcription activity compared to that resulting from the promoter in the absence of the enhancer. Enhancers may function upstream, within, or downstream of a gene, even as far away as 50 kilobases from the transcriptional initiation site. Enhancers may also function independently of their orientation. By "transcriptional terminator" is intended a DNA sequence that includes a nucleotide base pair sequence necessary for reducing or eliminating transcription. By "polyadenylation signal" is intended a sequence that controls the termination of transcription and translation.

Regulatory sequences for use in plants may be cloned from soybean by designing one or more PCR primers based on the sequence of a plant gene, or a regulatory element. The method may comprise designing at least one primer capable of hybridizing to a nucleotide sequence from a plant, using the primer to amplify DNA from a soybean plant to create amplified DNA, and testing the amplified DNA for regulatory sequence activity. By "regulatory sequence activity" is intended the ability to effect the transcription or translation of a gene. It includes promoter activity, transcriptional enhancer activity, transcriptional termination activity, and polyadenylation activity. Methods to measure or test for promoter activity are well known in the art (see section entitled "Evaluation of Promoter Activity"). Methods to measure or test for enhancer activity are well known in the art (see, for example, U.S. Pat. Nos. 6,806,064, 6,818,757, and 6,784,289). Methods to measure or test for terminator activity are well known in the art (see, for example, U.S. Pat. No. 5,093,252). Methods to measure or test for polyadenylation activity are well known in the art (see, for example, U.S. Pat. No. 6,632,637).

Alternatively, regulatory elements may be identified and cloned by other approaches. For example, soybean genomic or subgenomic libraries could be constructed using BAC, cosmid or lambda vectors. The libraries could be probed using promoter elements from a plant. Alternatively the libraries could be probed using gene coding regions from a plant. The resulting clones could be sequenced and the cis-acting elements surrounding the soybean coding regions determined. Alternatively, fragments from the coding regions of various soybean genes could be amplified from genomic DNA by PCR using primers designed from conserved regions of plant genes, such as conserved regions from maize. The soybean coding region fragments could then be used to probe genomic libraries as described.

Cis-acting elements could be cloned using inverse PCR. Sequence of soybean gene coding regions could be obtained as described above, then PCR primers designed and inverse PCR used to clone DNA flanking the coding regions using techniques well known in the art.

Antisense

The heterologous nucleotide sequence that is operably linked to the soybean promoter disclosed herein may be an antisense nucleotide sequence for a targeted gene. By "antisense nucleotide sequence" is intended a sequence that is in inverse orientation to the 5'-to-3' normal orientation of that nucleotide sequence. Expression of an antisense DNA sequence in a plant cell prevents the normal expression of the targeted gene. The antisense nucleotide sequence encodes an RNA transcript that is complementary to and capable of hybridizing to the endogenous messenger RNA (mRNA) produced by transcription of the targeted gene. In this way, production of the native protein encoded by the targeted gene is inhibited and a desired phenotypic response is achieved. Modifications of the antisense sequences may be made as long as the sequences hybridize to and interfere with expression of the corresponding mRNA. Antisense constructions having about 70%, 80%, 85%, 90% or 95% sequence identity to the corresponding antisense sequences may be used. Furthermore, portions of the antisense nucleotides may be used to disrupt the expression of the target gene. Generally, sequences of at least 50 contiguous nucleotides, 100 contiguous nucleotides, 200 contiguous nucleotides, or greater may be used. Thus, the promoter sequences disclosed herein may be operably linked to antisense DNA sequences to reduce or inhibit expression of a native protein in the plant.

Plant Expression Cassettes and Transformation Vectors

Transformation of plant cells can be accomplished by one of several techniques known in the art. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The promoter sequence of the invention may be provided in an expression cassette that allows it to drive expression of a heterologous sequence of interest in plant cells. By "expression cassette" is intended a DNA construct that is capable of resulting in the expression of a protein from an open reading frame in a cell. The cassette will include in the 5'-3' direction of transcription, a transcriptional initiation region comprising one of the promoter nucleotide sequences disclosed herein, or variants or fragments thereof, operably-linked to a heterologous sequence of interest, and a translational and transcriptional termination region (i.e., termination region) functional in plants. The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the heterologous sequence of interest to be under the transcriptional regulation of the regulatory regions.

Often, such constructs will also contain 5' and 3' untranslated regions. Such constructs may also contain a translated "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence. Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region comprising the promoter nucleotide sequence of the present invention, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) of interest may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing plant-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide or signal sequence to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. By "introducing" is intended to present to the organism being transformed the nucleotide construct in such a manner that the construct gains access to the interior of at least one cell of the organism.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication.

The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest. In various embodiments, the promoter of the invention can be used to drive expression of one or more genes described in the patent publications listed on Table 1, the contents of which are herein incorporated by reference in their entirety.

TABLE 1

| Trait | Reference |
| --- | --- |
| Water use efficiency | WO2000/073475 |
| | WO2009/150541 |
| | WO2009/150541 |
| | WO2012075429 |
| | WO2012077020 |
| Nitrogen use efficiency | WO1995/009911 |
| | WO1997/030163 |
| | WO2007/092704 |
| | WO2007/076115 |
| | WO2005/103270 |
| | WO2002/002776 |
| | WO2008/051608 |
| | WO2008/112613 |
| | WO2009/015096 |
| | WO2009/061776 |
| | WO2009/105492 |
| | WO2009/105612 |
| | WO2009/117853 |
| | WO2010/006010 |
| | WO2009/117853 |
| | WO2009/061776 |
| | WO2009/015096 |
| | WO2009/105492 |
| | WO2009/105612 |
| | WO2010/053621 |
| | WO2010/053867 |
| | WO2010/077890 |
| | WO2010/086220 |
| | WO2010/111568 |
| | WO2010/140388 |
| | WO2010/007496 |
| | WO2011/022597 |
| | WO2011/022608 |
| | WO2012087140 |
| Improved photosynthesis | WO2008/056915 |
| | WO2004/101751 |
| Nematode resistance | WO1995/020669 |
| | WO2001/051627 |
| | WO2008/139334 |
| | WO2008/095972 |
| | WO2006/085966 |
| | WO2003/033651 |
| | WO1999/060141 |
| | WO1998/012335 |
| | WO1996/030517 |
| | WO1993/018170 |
| | WO2008/095886 |
| | WO2008/095887 |

TABLE 1-continued

| Trait | Reference |
| --- | --- |
| | WO2008/095888 |
| | WO2008/095889 |
| | WO2008/095910 |
| | WO2008/095911 |
| | WO2008/095916 |
| | WO2008/095919 |
| | WO2008/095969 |
| | WO2008/095970 |
| | WO2008/095972 |
| | WO2008/110522 |
| | WO2008/139334 |
| | WO2008/152008 |
| | WO2010/077858 |
| | WO2010/091230 |
| | WO2010/102172 |
| | WO2010/106163 |
| | WO2011/082217 |
| | WO2011/003783 |
| Reduced pod dehiscence | WO2006/009649 |
| | WO2004/113542 |
| | WO1999/015680 |
| | WO1999/000502 |
| | WO1997/013865 |
| | WO1996/030529 |
| | WO1994/023043 |
| Aphid resistance | WO2006/125065 |
| | WO1997/046080 |
| | WO2008/067043 |
| | WO2004/072109 |
| | WO2009/091860 |
| | WO2010036764 |
| Sclerotinia resistance | WO2006/135717 |
| | WO2006/055851 |
| | WO2005/090578 |
| | WO2005/000007 |
| | WO2002/099385 |
| | WO2002/061043 |
| Botrytis resistance | WO2006/046861 |
| | WO2002/085105 |
| Bremia resistance | US 20070022496 |
| | WO2000/063432 |
| | WO2004/049786 |
| | WO2009/111627 |
| | WO2009/111627 |
| Erwinia resistance | WO2004/049786 |
| Closterovirus resistance | WO2007/073167 |
| | WO2007/053015 |
| | WO2002/022836 |
| Stress tolerance (including drought tolerance) | WO2010/019838 |
| | WO2009/049110 |
| | WO2008/002480 |
| | WO2005/033318 |
| | WO2008/002480 |
| | WO2008/005210 |
| | WO2008/006033 |
| | WO2008/008779 |
| | WO2008/022486 |
| | WO2008/025097 |
| | WO2008/027534 |
| | WO2008/027540 |
| | WO2008/037902 |
| | WO2008/046069 |
| | WO2008/053487 |
| | WO2008/057642 |
| | WO2008/061240 |
| | WO2008/064222 |
| | WO2008/064341 |
| | WO2008/073617 |
| | WO2008/074025 |
| | WO2008/076844 |
| | WO2008/096138 |
| | WO2008/110848 |
| | WO2008/116829 |
| | WO2008/117537 |
| | WO2008/121320 |
| | WO2008/125245 |
| | WO2008/142034 |
| | WO2008/142036 |

TABLE 1-continued

| Trait | Reference |
|---|---|
| | WO2008/150165 |
| | WO2008/092935 |
| | WO2008/145675 |
| | WO2009/010460 |
| | WO2009/016240 |
| | WO2009/031664 |
| | WO2009/038581 |
| | WO2009/049110 |
| | WO2009/053511 |
| | WO2009/054735 |
| | WO2009/067580 |
| | WO2009/073605 |
| | WO2009/077611 |
| | WO2009/079508 |
| | WO2009/079529 |
| | WO2009/083958 |
| | WO2009/086229 |
| | WO2009/092009 |
| | WO2009/094401 |
| | WO2009/094527 |
| | WO2009/102965 |
| | WO2009/114733 |
| | WO2009/117448 |
| | WO2009/126359 |
| | WO2009/126462 |
| | WO2009/129162 |
| | WO2009/132057 |
| | WO2009/141824 |
| | WO2009/148330 |
| | WO2010/055024 |
| | WO2010/058428 |
| | WO2010/064934 |
| | WO2010/076756 |
| | WO2010/083178 |
| | WO2010/086221 |
| | WO2010/086277 |
| | WO2010/101818 |
| | WO2010/104848 |
| | WO2010/118338 |
| | WO2010/120017 |
| | WO2010/120054 |
| | WO2010/121316 |
| | WO2010/127579 |
| | WO2010/134654 |
| | WO2010/139993 |
| | WO2010/039750 |
| | WO2011/034968 |
| | WO2011/001286 |
| | WO2011/017492 |
| | WO2011/018662 |
| | WO2011/024065 |
| | WO2011/038389 |
| | WO2011/46772 |
| | WO2011/053897 |
| | WO2011/052169 |
| | WO2011/063706 |
| | WO2011/067745 |
| | WO2011/079277 |
| | WO2011/080674 |
| | WO2011/083290 |
| | WO2011/083298 |
| | WO2011/091764 |
| | WO2011/052169 |
| | WO2011/053897 |
| | WO2011/056769 |
| | WO2011/063706 |
| | WO2011/067745 |
| | WO2011/083290 |
| | WO2011/083298 |
| | WO2011/091764 |
| | WO2011/096609 |
| | WO2011/122761 |
| Tobamovirus resistance | WO2006/038794 |
| | WO2009086850 |
| Yield | WO2010/046221 |
| | WO2010/046471 |
| | WO2010/049897 |
| | WO2010/055837 |

TABLE 1-continued

| Trait | Reference |
|---|---|
| | WO2010/065867 |
| | WO2010/069847 |
| | WO2010/075143 |
| | WO2010/075243 |
| | WO2010/100595 |
| | WO2010/102220 |
| | WO2010/104092 |
| | WO2010/108836 |
| | WO2010/120862 |
| | WO2010/123667 |
| | WO2010/124953 |
| | WO2010/125036 |
| | WO2010/127969 |
| | WO2010/129501 |
| | WO2010/140388 |
| | WO2010/140672 |
| | WO2011/011273 |
| | WO2011/000466 |
| | WO2011/003800 |
| | WO2011/006717 |
| | WO2011/008510 |
| | WO2011/009801 |
| | WO2011/011412 |
| | WO2011/015985 |
| | WO2011/020746 |
| | WO2011/021190 |
| | WO2011/025514 |
| | WO2011/025515 |
| | WO2011/025516 |
| | WO2011/025840 |
| | WO2011/031680 |
| | WO2011/036160 |
| | WO2011/036232 |
| | WO2011/041796 |
| | WO2011/044254 |
| | WO2011/048009 |
| | WO2011/053898 |
| | WO2011/051120 |
| | WO2011/058029 |
| | WO2011/061656 |
| | WO2011/085062 |
| | WO2011/088065 |
| | WO2011/053898 |
| | WO2011/058029 |
| | WO2011/061656 |
| | WO2011/085062 |
| | WO2011/088065 |
| | WO2011/095958 |
| | WO2011/097215 |
| | WO2011/099006 |
| | WO2011/104128 |
| | WO2011/104141 |
| | WO2011/104143 |
| | WO2011/104155 |
| | WO2011/106734 |
| | WO2011/106794 |
| | WO2011/109661 |
| | WO2011/114279 |
| | WO2011/114305 |
| | WO2011/114312 |
| | WO2011/114313 |
| | WO2011/117800 |
| | WO2011/135527 |
| | WO2011/136909 |
| | WO2011/139431 |
| | WO2011/140329 |
| | WO2011/146754 |
| | WO2011/147826 |
| | WO2011/157976 |
| | WO2011/161617 |
| | WO2011/161620 |
| | WO2011/109618 |
| | WO2011/159452 |
| | WO2012078949 |
| | WO2012083219 |
| | WO2012084742 |
| | WO2012084756 |
| | WO2012087903 |

TABLE 1-continued

| Trait | Reference |
|---|---|
| | WO2012087940 |
| | WO2012090500 |
| | WO2012091939 |
| | WO2012092106 |
| | WO2012092327 |
| | WO2012092573 |
| | WO2012092580 |
| | WO2012092596 |
| | WO2012093032 |
| | WO2012093833 |
| | WO2012097720 |
| | WO2012098517 |
| | WO2012102999 |
| | WO2012106321 |
| Oil content/composition | WO2010/045324 |
| | WO2010/053541 |
| | WO2010/130725 |
| | WO2010/140682 |
| | WO2011/006948 |
| | WO2011/049627 |
| | WO2011/060946 |
| | WO2011/062748 |
| | WO2011/064181 |
| | WO2011/064183 |
| | WO2011/075716 |
| | WO2011/079005 |
| | WO2011/049627 |
| | WO2011/062748 |
| | WO2011/064181 |
| | WO2011/064183 |
| | WO2011/079005 |
| | WO2011/146524 |
| | WO2011/161093 |
| | WO2011/163557 |
| | WO2011/163632 |
| | WO2011/163632 |
| | WO2012074385 |
| | WO2012074386 |
| | WO2012103452 |
| Biopharmaceutical production | WO2010/121818 |
| | WO2011/119115 |
| Improved recombination | WO2010/071418 |
| | WO2010/133616 |
| plant appearance | WO2010/069004 |
| | WO2011/060552 |
| Disease control (other) | WO2010/059558 |
| | WO2010/075352 |
| | WO2010/075498 |
| | WO2010/085289 |
| | WO2010/085295 |
| | WO2010/085373 |
| | WO2009/000736 |
| | WO2009/065863 |
| | WO2009/112505 |
| | WO2010/089374 |
| | WO2010/120452 |
| | WO2010/123904 |
| | WO2010/135782 |
| | WO2011/025860 |
| | WO2011/041256 |
| | WO2011/031006 |
| | WO2011/031922 |
| | WO2011/075584 |
| | WO2011/075585 |
| | WO2011/075586 |
| | WO2011/075587 |
| | WO2011/075588 |
| | WO2011/084622 |
| | WO2011/084626 |
| | WO2011/084627 |
| | WO2011/084629 |
| | WO2011/084630 |
| | WO2011/084631 |
| | WO2011/084314 |
| | WO2011/084324 |
| | WO2011/023571 |
| | WO2011/040880 |
| | WO2011/082304 |
| | WO2011/003783 |
| | WO2011/020797 |
| | WO2011/069953 |
| | WO2011/075584 |
| | WO2011/075585 |
| | WO2011/075586 |
| | WO2011/075587 |
| | WO2011/075588 |
| | WO2011/084314 |
| | WO2011/084324 |
| | WO2011/084622 |
| | WO2011/084626 |
| | WO2011/084627 |
| | WO2011/084629 |
| | WO2011/084630 |
| | WO2011/084631 |
| | WO2011/133892 |
| | WO2011/133895 |
| | WO2011/133896 |
| | WO2011/082217 |
| | WO2011/104153 |
| | WO2011/082304 |
| | WO2011/100650 |
| | WO2011/158242 |
| | WO2012003207 |
| | WO2012004013 |
| | WO2012004401 |
| | WO2012006271 |
| | WO2012006426 |
| | WO2012006439 |
| | WO2012006443 |
| | WO2012006622 |
| | WO2012007916 |
| | WO2012007919 |
| | WO2012009551 |
| | WO2012011034 |
| | WO2012012403 |
| | WO2012015039 |
| | WO2012058266 |
| | WO2012058458 |
| | WO2012058528 |
| | WO2012058730 |
| | WO2012061513 |
| | WO2012063200 |
| | WO2012065166 |
| | WO2012065219 |
| | WO2012066008 |
| | WO2012067127 |
| | WO2012068966 |
| | WO2012071039 |
| | WO2012071040 |
| Herbicide tolerance | U.S. Pat. No. 4,761,373 |
| | U.S. Pat. No. 5,304,732 |
| | U.S. Pat. No. 5,331,107 |
| | U.S. Pat. No. 5,718,079 |
| | U.S. Pat. No. 6,211,438 |
| | U.S. Pat. No. 6,211,439 |
| | U.S. Pat. No. 6,222,100 |
| | US 2003/0217381 |
| | US 2003/0217381 |
| | WO2004/106529 |
| | WO2000/27182 |
| | WO2005/20673 |
| | WO2001/85970 |
| | U.S. Pat. No. 5,545,822 |
| | U.S. Pat. No. 5,736,629 |
| | U.S. Pat. No. 5,773,703, |
| | U.S. Pat. No. 5,773,704 |
| | U.S. Pat. No. 5,952,553 |
| | U.S. Pat. No. 6,274,796 |
| | WO2004/106529 |
| | WO2004/16073 |
| | WO2003/14357 |
| | WO2003/13225 |
| | WO2003/14356 |
| | U.S. Pat. No. 5,188,642 |
| | U.S. Pat. No. 4,940,835 |
| | U.S. Pat. No. 5,633,435 |

TABLE 1-continued

| Trait | Reference |
|---|---|
| | U.S. Pat. No. 5,804,425 |
| | U.S. Pat. No. 5,627,061. |
| | U.S. Pat. No. 5,646,024 |
| | U.S. Pat. No. 5,561,236 |
| | U.S. Pat. No. 6,333,449 |
| | U.S. Pat. No. 6,933,111 |
| | U.S. Pat. No. 6,468,747. |
| | U.S. Pat. No. 6,376,754 |
| | U.S. Pat. No. 7,105,724 |
| | U.S. Pat. No. 7,105,724 |
| | WO2008/051633 |
| | U.S. Pat. No. 7,105,724 |
| | U.S. Pat. No. 5,670,454 |
| | U.S. Pat. No. 7,105,724 |
| | U.S. Pat. No. 7,105,724 |
| | U.S. Pat. No. 7,105,724 |
| | U.S. Pat. No. 7,105,724 |
| | U.S. Pat. No. 5,670,454 |
| | U.S. Pat. No. 7,105,724 |
| | U.S. Pat. No. 7,105,724 |
| | U.S. Pat. No. 7,105,724 |
| | U.S. Pat. No. 5,670,454 |
| | U.S. Pat. No. 7,105,724 |
| | U.S. Pat. No. 7,105,724 |
| | U.S. Pat. No. 7,105,724 |
| | U.S. Pat. No. 7,105,724 |
| | U.S. Pat. No. 6,153,401 |
| | U.S. Pat. No. 6,100,446 |
| | WO2005/107437 |
| | U.S. Pat. No. 5,670,454 |
| | U.S. Pat. No. 5,608,147 |
| | U.S. Pat. No. 5,670,454 |
| | WO2004/055191 |
| | WO199638567 |
| | U.S. Pat. No. 6,791,014 |
| | US 2002/0073443, |
| | US 20080052798 |
| | WO2011/022470 |
| | WO2011/034936 |
| | WO2011/028832 |
| | WO2011/028833 |
| | WO2011/028836 |
| | WO2011/068567 |
| | WO2011/076345 |
| | WO2011/085221 |
| | WO2011/094199 |
| | WO2011/094205 |
| | WO2011/068567 |
| | WO2011/085221 |
| | WO2011/094199 |
| | WO2011/094205 |
| | WO2011/145015 |
| | WO2012047595 |
| | WO2012048124 |
| | WO2012048136 |
| | WO2012048807 |
| | WO2012049663 |
| | WO2012050962 |
| | WO2012056401 |
| | WO2012057466 |
| | WO2012057465 |
| | WO2012058223 |
| plant metabolism | WO2011/060920 |
| | WO2011/119115 |
| | WO2011/102394 |
| reproduction | WO2011/113839 |
| Biofuels | WO2012073493 |
| Fruit ripening | WO2012073494 |
| Fiber quality | WO2012074386 |

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science*

13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.
Plants The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.
Evaluation of Plant Transformation Following introduction of heterologous foreign DNA into plant cells, the transformation or integration of heterologous DNA in the plant genome is confirmed by various methods such as analysis of nucleic acids or proteins and metabolites associated with the integrated DNA.

PCR analysis is a rapid method to screen transformed cells, tissue or shoots for the presence of incorporated DNA at the earlier stage before transplanting into the soil (Sambrook and Russell, 2001. *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}$P target DNA fragment to confirm the integration of introduced DNA in the plant genome according to standard techniques (Sambrook and Russell, 2001, supra).

In Northern blot analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by a heterologous gene operably linked to the TripPro5 promoter is then tested by hybridizing the filter to a radioactive probe derived from the heterologous gene, by methods known in the art (Sambrook and Russell, 2001, supra).
Evaluation of Promoter Activity Numerous methods are available to assess promoter activity in plants. Promoter function during expression of a gene of interest under its regulatory control may be tested at either the transcriptional or translational stage. At the transcriptional stage, RNA levels may be tested by DNA-RNA hybridization assays (i.e., Northern blot analysis), competitive reverse transcriptase PCR and RNAse protection assays. At the translational stage promoter activity may be determined by using specific functional assays for the protein synthesized (for example, by enzymatic activity or by immunoassay of the protein). For example, reporter gene activity, such as β-glucuronidase activity, luciferase activity or GFP fluorescence may be monitored at various times after transformation. Reporter gene activity may be monitored by enzymatic activity, by staining cells or tissue with substrate for the enzyme encoded by the reporter gene or by direct visualization under an appropriate wavelength of light (see, for example, Wang et al. (2000) *Plant Science* 156:201-211). Western blot may be carried out on the transgenic plants to confirm the presence of protein encoded by a gene of interest operably linked to the TripPro5 promoter by standard procedures (Sambrook and Russell, 2001, supra) using antibodies that bind to one or more epitopes present on the protein. Full-length promoter sequences, deletions and mutations of the promoter sequence may be assayed and their expression levels compared. See, for example, U.S. Pat. No. 6,072,050; and Sambrook et al. (1989) *Molecular Cloning: A Laboratory Manual* (2d ed., Cold Spring Harbor Laboratory Press, Cold Spring Harbor, N.Y.), herein incorporated by reference.

The following examples are offered by way of illustration and not by way of limitation.

EXPERIMENTAL

Example 1. Identification of Constitutive Promoters from Soybean

Public soybean transcriptome databases were used to identify genes that are highly expressed in different tissues (leaves, pod, flowers, roots, etc). The promoter regions (upstream of the first ATG) of these genes were PCR amplified from soybean genomic DNA (Jack) and linked to the luciferase gene coding region and a PinII terminator. These promoter-containing vectors were transformed into *Agrobacterium*. The transformed *Agrobacterium* were used to infiltrate young soybean or phaseolus leaf discs. After 2 days of incubation at 25° C. under 16 hr of light, the leaf discs were homogenized in PBS buffer for protein extraction. Soluble proteins were then assayed for luciferase activity using Promega's STEADY-GLO® Luciferase Assay System. Luciferase activity, average of three independent sets of infiltrated soybean leaf discs for each vector, is shown in FIG. 1. Pbdc6 and Pbdc7 showed comparable activity with Pubi3 from *Arabidopsis*. Pbdc6 (SEQ ID NO:1) was obtained from Glyma03g34310 which encodes a gamma tonoplast intrinsic protein. Pbdc7 (SEQ ID NO:2) was obtained from Glyma23g42220 which encodes a plasma membrane intrinsic protein.

Example 2. In Planta Analysis

DNA sequences carrying promoters Pbdc6 and Pbdc7, respectively, were cloned into pSZ8133 to link these promoters with grg23Ace5. The resulting binary vectors, pSZ8806 and pSZ8807, were transformed into *agrobacterium* LBA4404 and used to generate transgenic soybean plants. About 150 transgenic events of each vector were assayed with 4× glyphosate spray. Resistance to 4× glyphosate was scored one week after the spray (Table 2, 0 means no resistance and 4 represents the strongest resistance). UBQ3 was used as a control. Again Pbdc6 and Pbdc7 showed comparable strength with Pubi3At.

TABLE 2

| Resistance to 4x glyphosate (represented as percentage of plants scoring in each of the categories) | | | | | | |
|---|---|---|---|---|---|---|
| Vectors | promoters | 0 | 1+ | 2+ | 3+ | 2+ or 3+ |
| pSZ8133 | Pubi3At | 50% | 14% | 20% | 16% | 36% |
| pSZ8806 | Pbdc6 | 54% | 8% | 24% | 14% | 39% |
| pSZ8807 | Pbdc7 | 44% | 13% | 21% | 22% | 43% |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An expression cassette comprising a nucleic acid molecule comprising a nucleotide sequence operably linked to a heterologous nucleic acid, wherein said nucleotide sequence is selected from the group consisting of:
   the nucleotide sequence set forth in SEQ ID NO:2; and
   (b) a nucleotide sequence having at least 99% sequence identity to the sequence set forth in SEQ ID NO:2, wherein said sequence initiates transcription of the heterologous nucleic acid in a plant cell.

2. A vector comprising the expression cassette of claim 1.

3. A plant cell having stably incorporated into its genome the expression cassette of claim 1, wherein said nucleotide sequence is operably linked to a heterologous nucleic acid of interest.

4. The plant cell of claim 3, wherein said plant cell is from a dicot plant.

5. The plant cell of claim 4, wherein said dicot plant is soybean.

6. A plant having stably incorporated into its genome the expression cassette of claim 1, wherein said nucleotide sequence is operably linked to a heterologous nucleic acid of interest.

7. The plant of claim 6, wherein said plant is a dicot plant.

8. The plant of claim 7, wherein said dicot is soybean.

9. Transgenic seed comprising the expression cassette of claim 1.

10. The plant of claim 6, wherein the heterologous nucleic acid of interest encodes a gene product that confers herbicide, salt, pathogen, or pest resistance.

11. A method for expressing a heterologous nucleic acid of interest in a plant, said method comprising introducing into the plant cell an expression cassette comprising a promoter operably linked to the heterologous nucleic acid of interest, wherein said promoter comprises a nucleotide sequence selected from the group consisting of:
   (a) the nucleotide sequence set forth in SEQ ID NO:2; and
   (b) a nucleotide sequence having at least 99% sequence identity to the sequence set forth in SEQ ID NO:2, wherein said nucleotide sequence initiates transcription of the heterologous nucleic acid of interest in the plant cell; and, regenerating a transformed plant from said plant cell, wherein said plant has stably incorporated into its genome said expression cassette.

12. The method of claim 11, wherein said plant is a monocot plant.

13. The method of claim 11, wherein said plant is a dicot plant.

14. The method of claim 12, wherein said monocot is maize.

15. The method of claim 11, wherein said heterologous nucleic acid encodes a gene product that confers herbicide tolerance or pest resistance.

16. A method for expressing a heterologous nucleic acid of interest in a plant cell, said method comprising introducing into the plant cell an expression cassette comprising a promoter operably linked to the heterologous nucleic acid of interest, wherein said promoter comprises a nucleotide sequence selected from the group consisting of:
   (a) the nucleotide sequence set forth in SEQ ID NO:2; and
   (b) a nucleotide sequence having at least 99% sequence identity to the sequence set forth in SEQ ID NO:2, wherein said sequence initiates transcription of the heterologous nucleic acid of interest in the plant cell.

17. The method of claim 16, wherein said plant cell is a monocot plant cell.

18. The method of claim 16, wherein said plant cell is a dicot plant cell.

19. The method of claim 17, wherein said monocot is maize.

20. The method of claim 16, wherein the heterologous nucleic acid encodes a gene product that confers herbicide tolerance or pest resistance.

* * * * *